Figure 1:
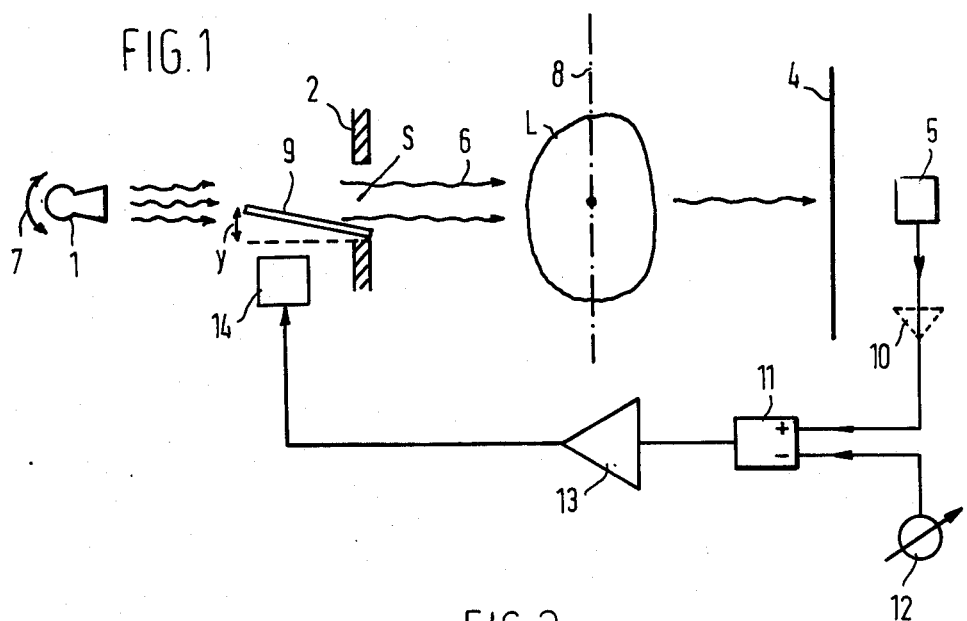

| United States Patent [19] | [11] Patent Number: 4,677,652 |
|---|---|
| Duinker et al. | [45] Date of Patent: Jun. 30, 1987 |

[54] APPARATUS FOR SLIT RADIOGRAPHY

[75] Inventors: Simon Duinker, Bloemendaal; Hugo Vlasbloem, Maasland, both of Netherlands

[73] Assignee: N.V. Optische Industrie "De Oude Delft", Netherlands

[21] Appl. No.: 729,617

[22] Filed: May 2, 1985

[30] Foreign Application Priority Data

May 3, 1984 [NL] Netherlands ............ 8401411

[51] Int. Cl.$^4$ ............................. G21K 1/04
[52] U.S. Cl. ............................. 378/151; 378/145; 378/147; 378/150; 378/153; 378/146
[58] Field of Search ............... 378/145–148, 378/150–153, 156–158

[56] References Cited

U.S. PATENT DOCUMENTS

| 3,755,672 | 8/1973 | Edholm et al. ............ 378/151 |
| 4,132,895 | 1/1979 | Froggatt ..................... 378/146 |
| 4,442,538 | 4/1984 | Haendle ..................... 378/146 |

FOREIGN PATENT DOCUMENTS 2345406 7/1975 Fed. Rep. of Germany ...... 378/150

Primary Examiner—Craig E. Church
Assistant Examiner—John C. Freeman
Attorney, Agent, or Firm—Louis E. Marn

[57] ABSTRACT

There is disclosed an improved control circuit for a slit radiographic apparatus wherein the slit radiographic apparatus is comprised of an X-ray source adapted to scan a body to be radiographed through a slit diaphragm with a planar fan beam wherein the slit diaphragm is divided into a plurality of attenuating sections each associated with a controllable X-ray attenuating member and wherein there is provided a detection assembly for detecting the intensity of the radiation having passed through the body and divided into sections corresponding to attenuating sections of the slit diaphragm wherein each X-ray attenuating member is controlled by the control circuit including an energizing circuit and a comparison circuit for each attenuating member of the slit diaphragm whereby the comparison circuit compares an output signal of an associated section of the detection means to a reference signal to form an output coupled to the energizing circuit to control the attenuating member of a respective attenuating section of the slit diaphragm so that the difference between the output signal of the section of the detection assembly and the reference signal continously pursues zero value.

5 Claims, 4 Drawing Figures

APPARATUS FOR SLIT RADIOGRAPHY

The invention relates to an apparatus for slit radiography comprising an X-ray source adapted to irradiate a body under examination through a slit diaphragm with a planar fan beam performing a scanning movement during operation, which slit diaphragm is divided into a plurality of juxtaposed sections; detection means for producing, during operation, electrical output signals and coacting with an X-ray detector mounted behind the body, which detection means are divided into sections corresponding to those of the slit diaphragm; and slit control means connected with the detection means for controlling X-ray attenuating elements coacting with each slit section.

By means of such an apparatus, which is disclosed in Dutch patent application 84,00845, the X-rays transmitted can be adjusted to the variations in absorption by the body under examination for each section of the slit diaphragm, whereby the quality of the final image can be enhanced considerably. In this manner, an image can be obtained that has sufficient contrast in both dark and light regions for allowing details to be seen well.

Dutch patent application 84,00845 discloses a number of embodiments in which either the position of the attenuation elements is controlled by generating a suitable magnetic field, or the attenuation elements are piezoelectric strips the position of which is determined by applying a suitable electrical voltage thereto. The instantaneous magnitude of the control signals adjusting the position of the attenuation elements is determined for each section by the difference between the signal from the detection means associated with the particular section and a predetermined reference signal.

Optimum operation of an apparatus of the above type requires an unambiguous relation between the control signal applied to the attenuation elements and the position of these elements, so that a reproducible adjustment of the position of the attenuation elements is achieved.

Controlling the position of the attenuation elements by means of a magnetic field has appeared to result in the occurrence of magnetic hysteresis effects. Reset springs coupled to the attenuation elements can exhibit (mechanical) hysteresis effects too. The same applies to attenuation elements in the form of spring reeds.

Furthermore, piezoelectric strips have likewise appeared to exhibit hysteresis effects.

Such hysteresis effects result in the absence of an unambiguous relation between the position of an attenuation element and the control signal. Furthermore, a reduction of the control signal to zero does not guarantee a return of the attenuation element into its rest position.

Consequently, there is a need for slit control means capable of bringing the attenuation elements into a position resulting in the desired attenuation at any desired moment, regardless of the occurrence of hysteresis effects.

It is an object of the invention to meet this need. To this end, in accordance with the invention an apparatus of the above type is characterized in that the slit control means include an energizing circuit for each pair of corresponding sections of the detection means and the slit, under the influence of which energizing circuit the position of at least one attenuation element coacting with the particular slit section is changed and which energizing circuit is included in a control circuit closed via the radiation passing through this slit section, penetrating through the body and incident upon the corresponding section of the detection means, which control circuit further includes a comparison circuit having its output coupled with the energizing circuit and having an electrical signal from the section of the detection means applied to its one input and a predetermined reference signal applied to its other input, the energizing circuit being so operated that the difference between the input signals of the comparison circuit continuously pursues zero value.

Figure 2:
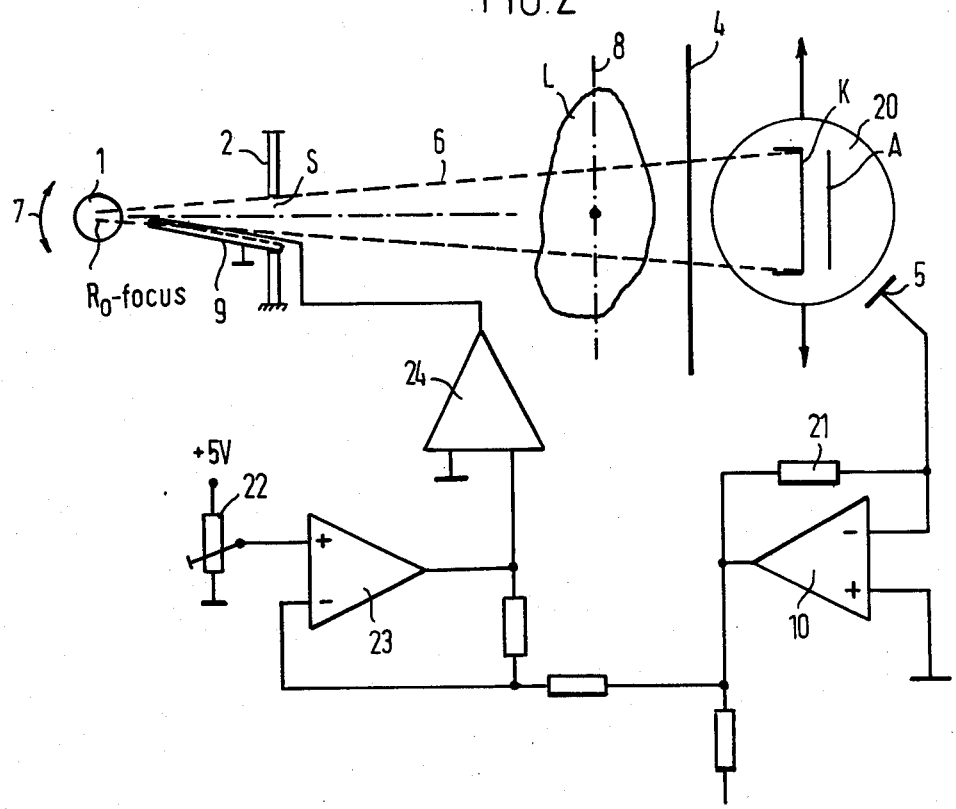
Figure 3A:
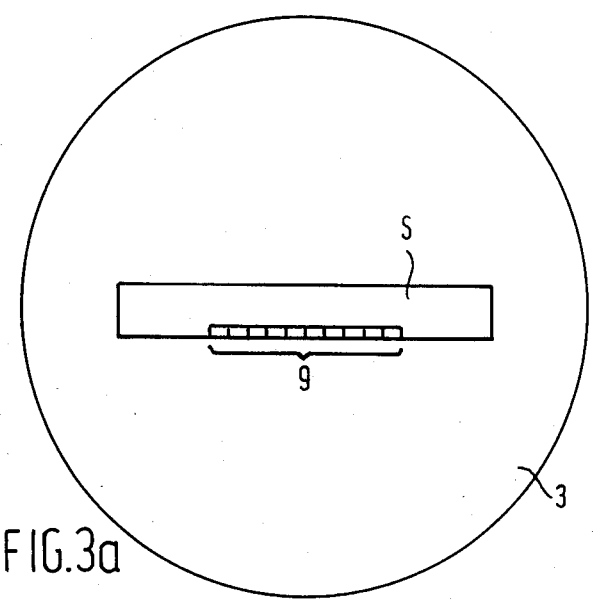
Figure 3B:
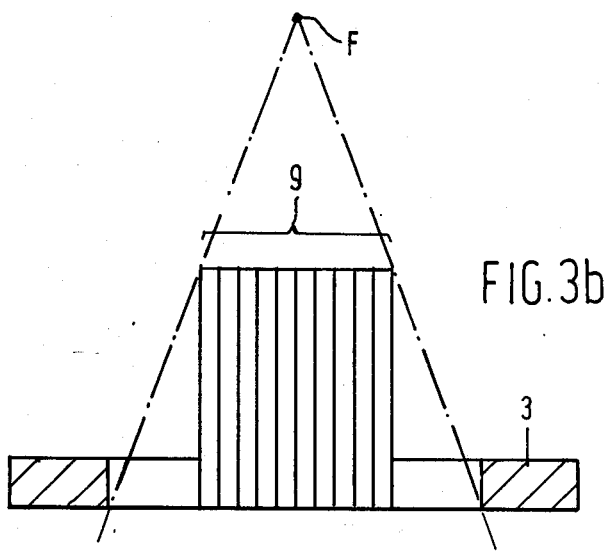

The invention will be described in greater detail hereinafter with reference to the accompanying drawings, in which:

FIG. 1 shows a basic diagram of an apparatus according to the invention;

FIG. 2 schematically shows an example of an apparatus for slit radiography including an embodiment of a control device according to the invention; and FIGS. 3a and 3b schematically show a front view and a cross-sectional view, respectively, of a slit diaphragm including attenuation elements in the form of reeds.

FIG. 1 shows a basic diagram of an apparatus according to the invention. The apparatus comprises an X-ray source 1 adapted to project X-rays onto a body L under examination through a slit diaphragm 2 consisting, for example, of a lead plate having an elongated slit S. In the drawing, the slit S extends normal to the plane of the drawing. A box is mounted behind body L, the X-ray transparent front plate of which box is schematically shown at 4. An X-ray detector not shown in this basic diagram is mounted behind front plate 4. Behind this plate 4 there are also mounted detection means 5 adapted to produce electrical signals, which signals are proportional at each moment to the X-rays incident upon the X-ray detector at that moment.

As the slit S is of elongated shape, a planar fan beam 6 is produced.

During operation, the body L under examination is scanned by means of this beam. Scanning can take place in a direction normal to the longitudinal direction of slit S. To this end, for example the assembly of slit diaphragm and X-ray source can swing about an axis extending normal to the plane of the drawings, as indicated by arrow 7.

However, scanning can be performed in other manners too. When using an X-ray source producing a conical X-ray beam, for example the source can be moved up and down relative to the diaphragm, if desired along a curved path, or the diaphragm can be moved up and down relative to the X-ray source, if desired along a curved path. It is further possible to move the assembly of X-ray source and slit diaphragm up and down, again, if desired, along a curved path.

Furthermore, should the apparatus be used for taking axial tomography pictures, scanning can take place in the plane of the fan beam by rotating the apparatus or the body about an axis 8 extending in the plane of the drawing and normal to the plane of the fan beam. A series of juxtaposed attenuation elements is mounted in or near slit S of the slit diaphragm, which series extends normal to the plane of the drawings. One of these attenuation elements is shown at 9. In actual practice, the slit is divided into a plurality, for example ten, juxtaposed sections each coacting with a suitable attenuation element. In the basic diagram of FIG. 1 only a single attenuation element is shown, which element is reed-shaped and has one free end, but such an element may be of any other suitable form, such as an element adapted for sliding movement into and out of the path of the X-ray beam, as disclosed, for example, in Dutch patent application 84,00845.

The detection means 5 include sections corresponding to the sections of the slit. FIG. 1 shows only a single section of the detection means. This section corresponds to the slit section associated with the attenuation element shown.

The detection means may be a series of juxtaposed photosensitive elements, which elements follow the scanning movement of the X-ray beam and are hence continuously able to collect the light produced by the X-ray detector and convert this light into an electrical signal. For example, photomultiplier tubes or silicon cells can be used as the photosensitive elements.

Each photosensitive element detects the light from an associated area of, for example, 4×4 cm of the X-ray detector.

Each section of the detection means is connected, if desired via a pre-amplifier 10 shown in broken lines in FIG. 1, to one input of a comparison circuit associated with the particular section, which comparison circuit is, for example, a differential amplifier 11. The other input of the comparison circuit is connected to an adjustable reference signal generator 12.

The output of the comparison circuit is connected, if desired via a separate amplifier 13, to an energizing circuit 14 for the associated attenuation element. Amplifier 13, however, may also be included in the comparison circuit.

As described in Dutch patent application 84,00845, the position of the attenuation elements can be changed in different manner. If the attenuation elements are cantilever piezoelectric strips, a voltage difference is generated between the electrodes of each strip. This voltage difference causes the strip to arch, so that its free end extends into the X-ray beam to a greater or lesser extent.

If the attenuation elements are cantilever spring reeds or pivoted rigid reeds, their position can be changed by energizing a magnet coil having a core extending to a point near the reeds. It is also possible to have the reeds each connected to a movable core of a magnet coil.

Having x designate the output signal of the energizing circuit and y designate the displacement of the attenuation element relative to the rest position, then y=f(x). As stated above, this relation is not unambiguous if hysteresis effects occur.

To eliminate the influence of hysteresis effects, the comparison circuit is arranged to produce a positive or negative output signal in response to the occurrence of a difference between the detector signal and the reference signal, which output signal is maintained until the detector signal is equal to the reference signal.

Consequently, the attenuation elements are not directly brought into the desired position in response to the application to the energizing circuit of a signal whose magnitude depends upon the difference between the detector signal and a reference value (steered operation), but a positive or negative (depending upon the sign of the difference between the detector signal and the reference signal) signal is applied to the energizing circuit, which signal is maintained as long as the detector signal differs from the reference signal (controlled operation).

In fact, a control circuit is obtained, which circuit is closed by the X-rays passing through the relevant section of the slit diaphragm and subsequently through the body and the radiation between the X-ray detector and the corresponding section of the detection means. The control circuit is continuously operative, with the help of the detection means, th compare the actual position of the attenuation elements with a desired position represented by the reference signal, the position of the attenuation elements being changed as soon as a deviation from the desired position has been established.

FIG. 2 schematically shows a practical embodiment of an apparatus according to the invention. Components of the apparatus shown in FIG. 2 which correspond to components of the apparatus shown in FIG. 1 are designated by the same reference symbols. FIG. 2 shows an example of an X-ray detector 20 mounted behind front plate 4, which detector is suited for use in practice and is shown in cross-sectional view. X-ray detector 20 is a known per se, elongate image intensifier tube of the proximity focus type, the cathode K of which is arranged in known per se manner for releasing electrons in response to X-rays incident thereon, which electrons are accelerated into the direction of the anode A. Anode A forms a light image from the electrons incident thereon, likewise in known per se manner. In a practical embodiment, the cathode can be, for example, 40 cm long and 4 cm wide. The apparatus should be provided with means causing the detector to move in synchronism with the scanning movement of the X-ray beam, so that radiation having passed through the body L is incident upon the cathode at all times. In turn, the detection means should follow the movement of the X-ray detector so as to be able to detect the light image formed by the anode. Additionally, this light image is recorded on, for example, a photographic plate or viewed by means of a video camera or a similar instrument in known per se manner.

It is also possible to employ an X-ray detector of the type shown which has its anode formed of a series of CCDs (charge-coupled devices) producing an electrical output signal containing the desired image data instead of an optical output signal, which data may be stored in a memory.

In that case, the detection means can be arranged to collect the electrical output signals and apply these signals to the comparison circuit.

Alternatively, a fluorescent screen can be mounted in front of the X-ray detector, which screen converts a small portion of the X-rays incident thereon into light, which light can be detected by means of photosensitive cells.

It is further possible to employ, instead of an elongate, narrow X-ray detector, an X-ray detector of dimensions sufficient for covering the entire area to be scanned, which detector can thus remain stationary. In that case, the detection means should be so mounted or movable that they cover the area of incidence of the planar fan beam on the X-ray detector at all times.

Each section of the detection means 5 in the embodiment shown in FIG. 2, consequently each photosensitive element, is connected to one input of an associated transimpedance amplifier (current-voltage amplifier) 10 having its other input connected to ground.

The gain can be controlled by means of a feedback resistor 21. The output voltage of amplifier 10 is a measure for the amount of X-radiation received by the X-ray detector in the area with which the detection element is associated.

The output voltage of amplifier 10 is compared with a reference voltage to be set by means of a potentiometer 22 corresponding to the reference signal generator 12 of FIG. 1. To this end, the output voltage of transimpedance amplifier 10 is applied to one input of a reference amplifier 23 corresponding to the comparison circuit 11 and the amplifier 13 of FIG. 1. The reference voltage is applied to the other input of reference amplifier 23.

If, as shown in the embodiment of FIG. 2, the attenuation elements 9 are piezoelectric strips, the output signal of the reference amplifier is applied to a voltage amplifier 24 corresponding to the energizing circuit 14 of FIG. 1. Voltage amplifier 24 can apply voltages in a range of, for example, from −300 volts to +300 volts to one of the electrodes of the associated piezoelectric strip 9. The other electrode of the piezoelectric strip is connected to ground.

If the position of the attenuation elements is influenced by magnet coils, amplifier 24 will be a current amplifier determining the magnitude of the current traversing the coil.

The most important element of the circuit arrangement is the comparison circuit in which the magnitude and polarity of the detector signal from the associated detection element are compared to those of the reference signal set. If the input voltage of the reference amplifier as supplied by the transimpedance amplifier is higher than the reference voltage set, this means that the amount of X-radiation at photosensitive cell 5 is too high and that the X-rays passed by the corresponding section of the slit diaphragm should be attenuated. In the situation shown in the drawing, piezoelectric strip 9 should then arch upwardly, which is accomplished by means of the output signal of the reference amplifier as supplied through voltage amplifier 24. As soon as the piezoelectric strip starts arching upwardly, the X-rays passing at this strip are (further) attenuated, which is detected by photosensitive cell 5. As a result, the output signal of this cell will decrease and so will, in turn, the input signal of the reference amplifier as supplied by the transimpedance amplifier.

This control process continues until the piezoelectric strip extends into the X-ray beam to such an extent that the reference signal is equal to the output signal of the transimpedance amplifier. The output signal of the voltage amplifier then remains constant until the photosensitive cell produces another output signal resulting in a difference between the input signals of the reference amplifier.

Analogously, the degree of arching of the piezoelectric strip is reduced if the output signal of the transimpedance amplifier applied to the one input of the reference amplifier is smaller than the reference voltage.

In this manner, the degree of arching of each piezoelectric strip is positively controlled in both directions and the results of hysteresis effects are effectively neutralized.

It will be clear to the worker in the art that the energizing current traversing a magnet coil, which coil houses a movable soft iron core connected with an attenuation element, can be positively controlled for both directions of movement of the attenuation element in a similar manner.

The level of the adjustable reference voltage corresponds to the mean value of the average exposure desired at each section of the X-ray detector.

After an initial adjustment, the reference voltages are constant for each section but may differ from each other to compensate for apparatus related parameters, for example, differences between the characteristics of the attenuation elements, inhomogeneities in the X-ray detector, differences between the detection elements, anisotropy of the X-ray beam produced by the X-ray source used, and like phenomena. Compensation for the lastnamed phenomenon is particularly important if the X-ray source and the diaphragm are moved relative to each other during the scanning movement, as in that case each time a different portion of the X-ray beam is effectively used.

FIGS. 3a and 3b schematically show a front view and a cross-sectional view, respectively, of an example of a slit diaphragm suitable for use in the apparatus according to the invention.

The slit diaphragm comprises a plate 3 impermeable to X-rays, for example a lead plate, in which an essentially rectangular, central slit S is formed.

In the example shown, ten juxtaposed, parallel reed or strip-shaped attenuation elements 9 are placed in the slit. The attenuation elements have their one ends secured in or near the slit and have their other ends facing the X-ray source, the X-ray focus of which is shown at F, which other ends can be caused to extend to a greater or lesser extent into the X-ray beam under the influence of the energizing circuit. Such an arrangement results in a compact structure but it is also possible, in principle, to have the free ends of the attenuation elements point away from the x-ray source, i.e. into the direction of the X-ray detector.

It is observed that, after the foregoing, different modifications of the embodiments described will be obvious to the worker in the art.

For example, also in the event that hysteresis effects do not play a significant part in the control of the position of the attenuation elements, self-evidently a control arrangement in accordance with the invention can be used.

Such modifications are considered to fall within the scope of the invention.

We claim:

1. An apparatus for slit radiography, which comprises:
   an X-ray source;
   an X-ray detector for collecting radiation passing through a body to be radiographed;
   a slit diaphragm positioned between said X-ray source and said body for forming a substantially planar X-ray beam;
   a plurality of attenuating elements positioned along said slit diaphragm so as to form a plurality of attenuating sections;
   means for scanning said body with said planar X-ray beam;
   detection means cooperating with said X-ray detector and comprising a plurality of response sections juxtaposed along a direction of said slit diaphragm, each of said response sections being responsive to radiation collected on said X-ray detector to produce an electric signal representative of intensity of thus collected radiation, each of said response sections of said detection means corresponding to a respective attenuating section of said plurality of attenuating sections; and
   means for simultaneously controlling each of said attenuating sections during scanning of said body in response to said electric signal produced at a respective response section and including a control circuit and an energizing circuit for said attenuating elements wherein said control circuit includes a comparison circuit having an output coupled to said energizing circuit, an electric signal from each response section and a predetermined reference signal being applied as inputs to said comparison circuit, said energizing circuit being operated so that the differences between said inputs to said comparison circuit continuously pursues zero value.

2. The apparatus as defined in claim 1 wherein said comparison circuit is a differential amplifier.

3. The apparatus as defined in claims 1 or 2 wherein said reference signal for said comparison circuit for each control circuit of respective attenuationg member is identical.

4. The apparatus as defined in claims 1 or 2 wherein said reference signal exhibits a predetermined difference dependent on apparatus-related parameters.

5. The apparatus as defined in claim 1 wherein said control circuit includes a transimpedance amplifier to which an electrical signal from an associated response section of said detection means is applied as an input and an output signal from the transimpedance amplifier is applied as one input to said comparison circuit.

* * * * *